United States Patent
Kral

(10) Patent No.: US 8,287,816 B2
(45) Date of Patent: Oct. 16, 2012

(54) MOBILE DEVICE FOR TRANSPORTING, TRACKING, AND PROCESSING MEDICAL INSTRUMENTS

(75) Inventor: Jude A. Kral, Twinsburg, OH (US)

(73) Assignee: American Sterilizer Company, Mentor, OH (US)

( * ) Notice: Subject to any disclaimer, the term of this patent is extended or adjusted under 35 U.S.C. 154(b) by 799 days.

(21) Appl. No.: 12/105,695

(22) Filed: Apr. 18, 2008

(65) Prior Publication Data

US 2009/0261549 A1 Oct. 22, 2009

(51) Int. Cl.
*A61L 2/00* (2006.01)
*A47B 97/00* (2006.01)

(52) U.S. Cl. ............................ 422/300; 422/1; 312/249.8

(58) Field of Classification Search .............. 422/1, 300; 312/249.8; 280/47.35
See application file for complete search history.

(56) References Cited

U.S. PATENT DOCUMENTS

| | | | | | |
|---|---|---|---|---|---|
| 4,299,244 A | * | 11/1981 | Hirai | ............................ | 134/102.1 |
| 4,336,858 A | * | 6/1982 | Loyzim | ............................ | 180/179 |
| 5,366,896 A | | 11/1994 | Margrey et al. | .................. | 436/48 |
| 5,443,801 A | * | 8/1995 | Langford | ...................... | 422/294 |
| 5,464,580 A | | 11/1995 | Popescu et al. | .................. | 422/34 |
| 6,543,983 B1 | | 4/2003 | Felder et al. | .................... | 414/402 |
| 6,814,932 B2 | * | 11/2004 | Hlebovy et al. | .................. | 422/28 |
| 2002/0161460 A1 | | 10/2002 | Noguchi | .......................... | 700/90 |
| 2004/0015266 A1 | | 1/2004 | Skoog | ............................ | 700/245 |
| 2004/0093650 A1 | | 5/2004 | Martins et al. | ..................... | 901/1 |
| 2004/0174261 A1 | | 9/2004 | Volpi et al. | ................. | 340/572.1 |
| 2005/0000553 A1 | | 1/2005 | Noguchi et al. | ................ | 134/84 |

OTHER PUBLICATIONS

Basch, "Surgical Instrument Tracking Systems," Infection Control Today, www. infectioncontroltoday.com/articles/0a1instrument. html, last date accessed Nov. 25, 2003.
Brock, "White Paper," Auto-ID Center Massachusetts Institute of Technology, Feb. 1, 2002, pp. 3-14.
McConnel, "RFID Will Change the Way We Live and Work," iApplianceWeb, www.iapplianceweb.com/story/OEG20030707S0083, last date accessed Nov. 24, 2003.

* cited by examiner

*Primary Examiner* — Kevin Joyner
(74) *Attorney, Agent, or Firm* — Kusner & Jaffe; Michael A. Centanni

(57) ABSTRACT

A mobile device for transporting, tracking and processing medical instruments. The device comprises a cart including at least one receptacle for receiving an instrument container having instruments stored therein. The cart also includes plumbing for circulating processing fluids through the instrument container and a communications system for communicating tracking data associated with the instrument container and the cart.

14 Claims, 4 Drawing Sheets

MOBILE DEVICE FOR TRANSPORTING, TRACKING, AND PROCESSING MEDICAL INSTRUMENTS

FIELD OF THE INVENTION

The present invention relates generally to the handling of medical instruments such as dental, pharmaceutical, veterinary, and mortuary devices; and the present invention relates more particularly to a mobile device for transporting, tracking and processing medical instruments.

BACKGROUND OF THE INVENTION

Medical instruments (such as dental, pharmaceutical, veterinary, and mortuary devices) that are exposed to blood or other bodily fluids require thorough cleaning and anti-microbial deactivation between each use. Typically, a plurality of medical instruments is assembled together as a kit for use in a specific medical procedure. The procedure is performed in a specific location, i.e., a procedure room located within a facility such as a hospital. During the procedure, the medical instruments are often soiled such that they are coated with biological matter, e.g., blood and tissue.

Typically, soiled medical instruments are placed in a container after being used during a procedure. A hospital staff member then transports the container from the procedure room to a cleaning room. In the cleaning room, the soiled medical instruments undergo a treatment process that includes a pre-cleaning step, a manual cleaning step, and a reprocessing step. During the pre-cleaning step, the instruments are moistened or hydrated to prevent biological matter, e.g., blood, tissue, etc. from drying prior to cleaning of the instruments. In the manual cleaning step, particulate matter and debris are removed from the instruments. In the reprocessing step, the instruments are microbially deactivated.

One problem related to cleaning soiled medical instruments is that biological matter coating the medical instruments begins to dry soon after use. As the biological matter dries, it adheres to the medical instruments and becomes difficult to remove. Therefore, it is desirable to perform the pre-cleaning step in a timely matter. Accordingly, the soiled medical instruments are preferably transported from the procedure room to the cleaning room with as little delay as possible.

However, delays can occur before and after the soiled medical instruments are transported to the cleaning room. For example, hospital staff may not be readily available to transport the soiled medical instruments to the cleaning room when needed. Any such delay that occurs before the instruments are exposed to the pre-cleaning step allows the coating of biological matter on the medical instruments to continue to dry and become increasingly difficult to remove.

The present invention overcomes this and other problems by providing a device that facilitates tracking and transport of a container while preventing drying of biological matter that coats medical instruments stored within the container.

SUMMARY OF THE INVENTION

In accordance with one embodiment of the present invention, there is provided a transport device for moving instruments to various locations within a facility (e.g., hospital), the transport device including a cavity for receiving an instrument container, and plumbing for circulating fluids through the container, thereby treating instruments located inside the container.

An advantage of the present invention is a transport device that is capable of transporting medical instruments.

Another advantage of the present invention is a transport device as described above having a cart that is dimensioned to receive a storage container for storing medical instruments.

Another advantage of the present invention is a transport device as described above that is capable of rinsing medical instruments.

Another advantage of the present invention is a transport device as described above that is capable of washing medical instruments.

Another advantage of the present invention is a transport device as described above that is capable of circulating a fluid through a container for treatment, e.g., pre-cleaning, washing, rinsing, hydrating, etc., of medical instruments stored therein.

Another advantage of the present invention is a transport device as described above that is capable of maintaining medical instruments in a moist environment to prevent drying of biological matter thereon.

Another advantage of the present invention is a transport device as described above that is capable of drying medical instruments stored within a container.

Another advantage of the present invention is a transport device as described above that is capable of obtaining data regarding a container for medical instruments.

Another advantage of the present invention is a transport device as described above that is capable of communicating data (e.g., location, status, identification of medical instruments contained therein, etc.) regarding a container for medical instruments to a central information system.

These and other advantages will become apparent from the following description of one embodiment taken together with the accompanying drawings and the appended claims.

BRIEF DESCRIPTION OF THE FIGURES

The invention may take physical form in certain parts and arrangement of parts, one embodiment of which will be described in detail in the specification and illustrated in the accompanying drawings which form a part hereof, and wherein.

DETAILED DESCRIPTION OF THE INVENTION

Figure 1:
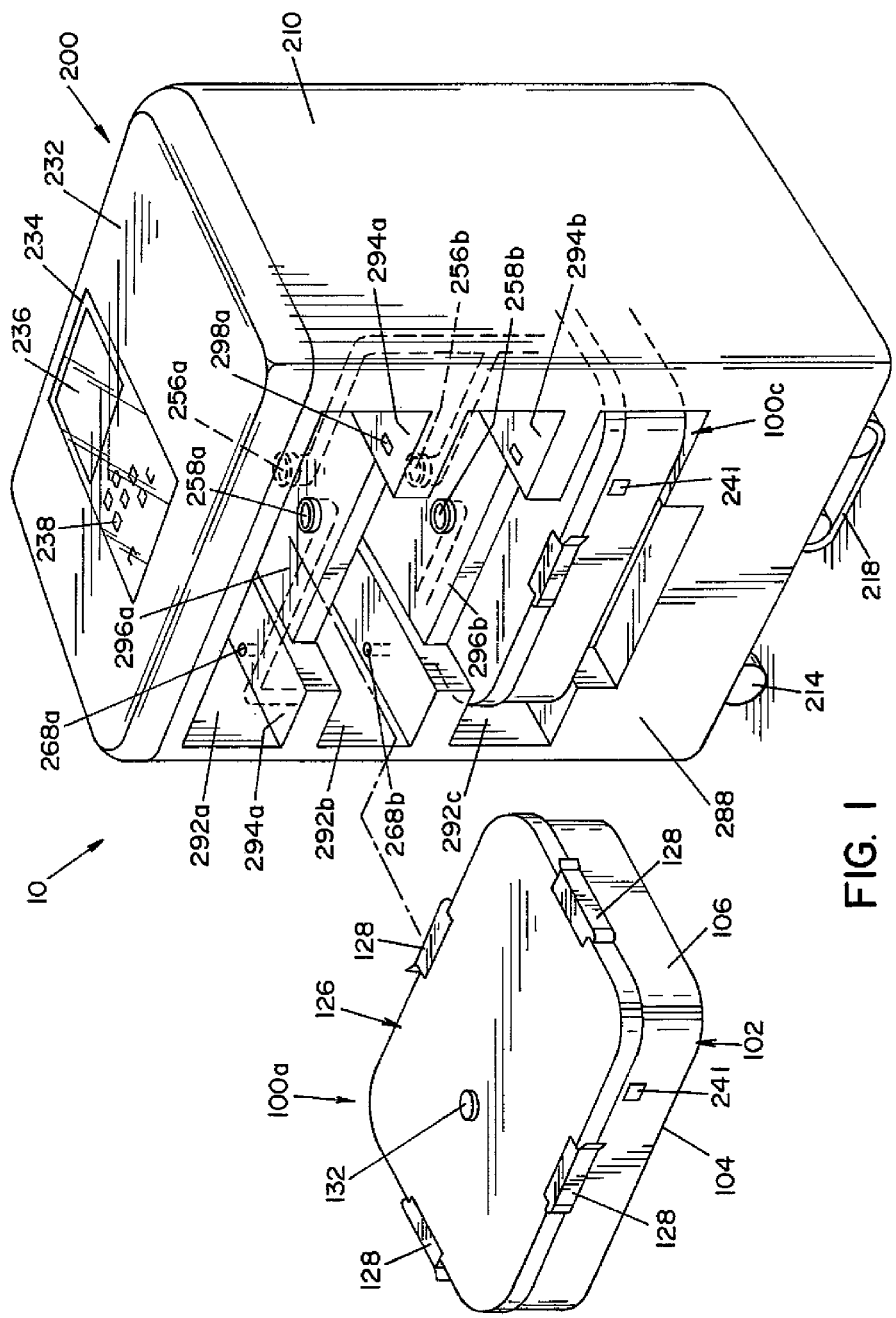
FIG. 1 is a perspective view of a transport device according to one embodiment of the present invention, wherein the transport device includes a cart having a plurality of receptacles for receiving storage containers for storing medical instruments.

Referring now to the drawings wherein the showings are for the purpose of illustrating one embodiment of the invention only and not for the purpose of limiting same, FIG. 1 shows a transport device 10 comprised of a cart 200 and at least one container 100 according to one embodiment of the present invention. In the illustrated embodiment, container 100 is dimensioned to receive one or more medical instruments 52. A plurality of medical instruments in each container 100 may form a kit 50. Cart 200 is dimensioned to receive container 100 such that container 100 is fluidly connected thereto, as will be described in detail below.

Figure 2:
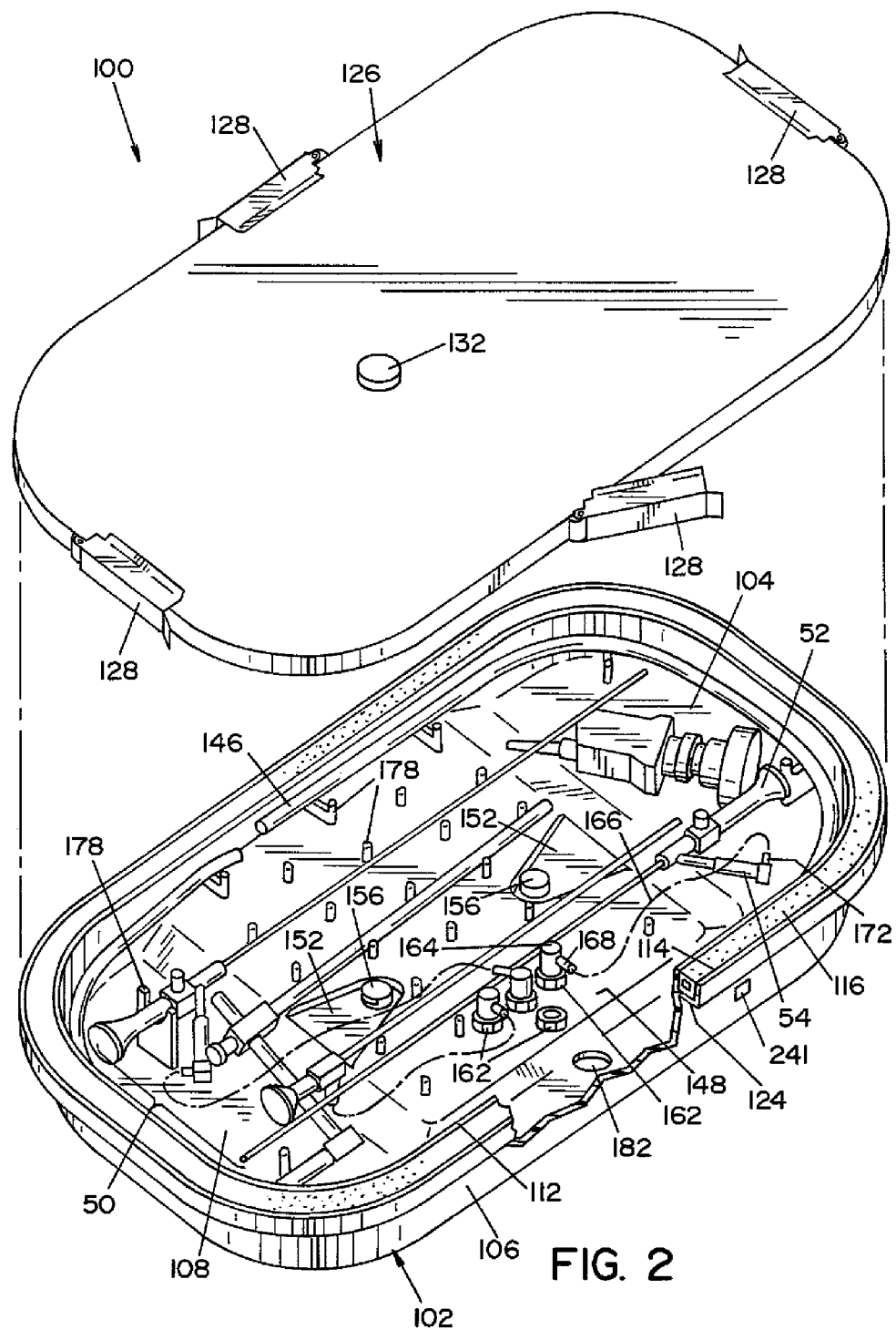
FIG. 2 is a perspective view of a storage container for storing medical instruments.

Referring now to FIG. 2, kit 50 is comprised of one or more medical instruments that are assembled together. The following description of the structure and operation of transport device 10 below can be understood in light of a typical medical instrument 52 of kit 50. Medical instrument 52 has a lumen, i.e., an internal passageway (not shown), defined therethrough and a port 54 defined at one end of the lumen. It should be appreciated that illustrated instruments 52 are exemplary, and are not intended to limit the scope of the present invention. For instance, some medical instruments may not include a lumen.

Referring now to FIGS. 1 and 2, container 100 includes a tray 102 and a lid 126. Tray 102 is generally cup-shaped and has a bottom wall 104 and a continuous side wall 106. Continuous side wall 106 is disposed around the periphery of bottom wall 104, and extends upward from bottom wall 104 to a top edge 112. A cavity 108 is defined within tray 102 by bottom wall 104 and continuous side wall 106. Cavity 108 of container 100 is dimensioned to receive one or more medical instruments such as medical instrument 52.

Figure 3:
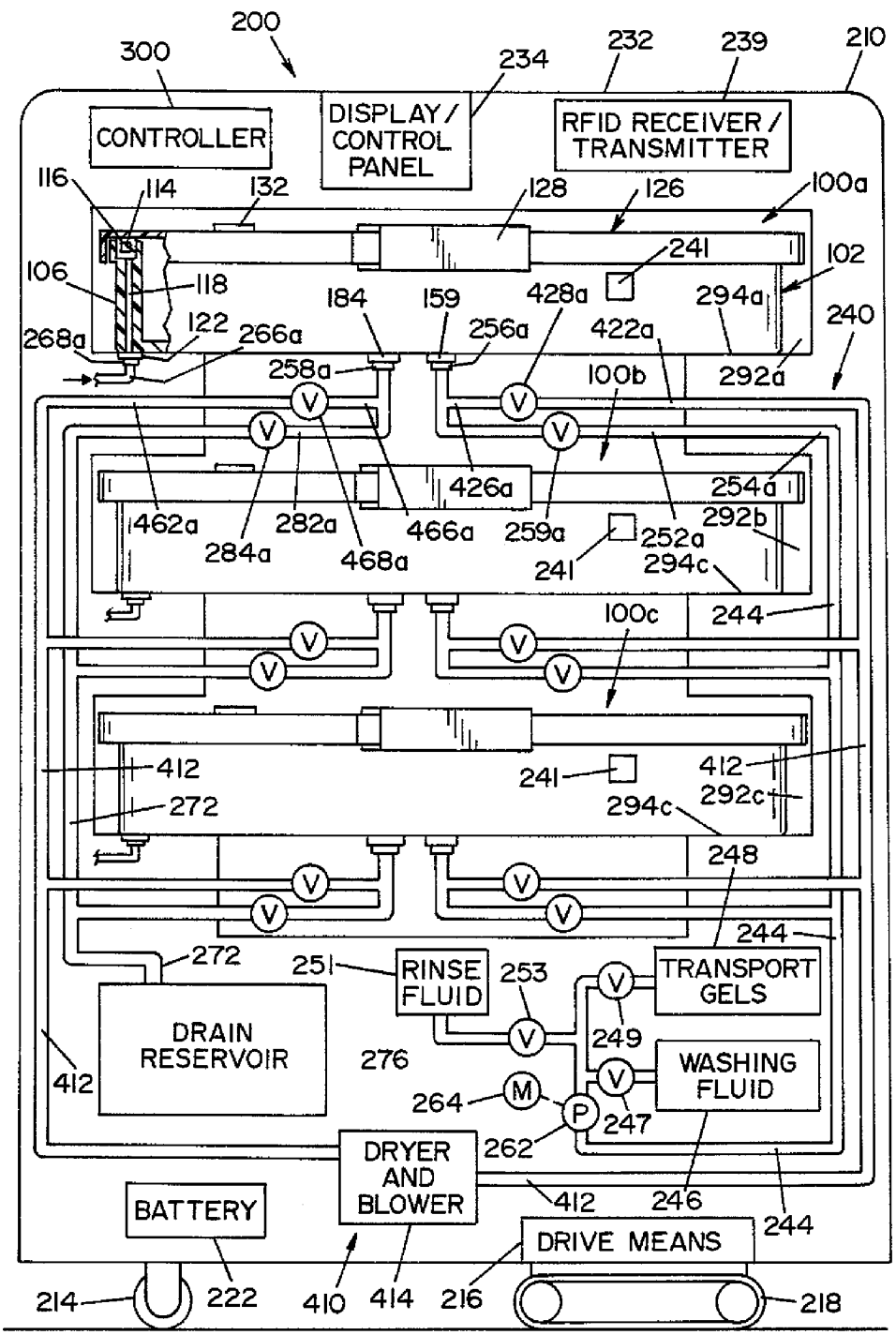
FIG. 3 is a schematic view of the transport device of FIG. 1, wherein storage containers are disposed within the plurality of receptacles of the cart.

A flange 124 is defined around top edge 112 of side wall 104. Flange 124 is generally perpendicular to side wall 106 and projects away from cavity 108. An open channel 114 is defined in flange 124 and is dimensioned to receive an inflatable seal 116. Referring now to FIG. 3, a gas conduit 118 for providing compressed gas, e.g., air, is defined within side wall 106 and extends from bottom wall 104 to inflatable seal 116. At one end, gas conduit 118 is fluidly connected to a gas supply port 122 defined in bottom wall 104 of tray 102. As will be discussed below, gas supply port 122 is connectable to a source (not shown) of compressed gas, e.g., air, for inflating inflatable seal 116.

A passage (not shown) is defined within bottom wall 104 of tray 102 for connecting cavity 108 and the lumen of medical instrument 52 to a circulation system 240 of cart 200, discussed below. The passage has a first end and a second end.

Bottom wall 104 of tray 102 is contoured and has an elevated portion 148 generally located in a central region thereof. A pair of recesses 152 are formed in elevated portion 148 of bottom wall 104. Each recess 152 has a spray nozzle 156 disposed therein for introducing fluid into cavity 108. A plurality of connection assemblies 162 is also formed in elevated portion 148 of bottom wall 104. Spray nozzles 156 and connection assemblies 162 are connected to the first end of the passage defined within bottom wall 104.

As can be seen in FIG. 3, an inlet port 159 is formed on bottom wall 104 of tray 102 outside of cavity 108 at the second end of the passage defined within bottom wall 104. In this respect, inlet port 159 is connected to spray nozzles 156 and connection assemblies 162 by the passage defined within bottom wall 104 of tray 102. Inlet port 159 is connectable to circulation system 240 of cart 200 as will be discussed further below.

Medical instrument 52 is connectable to circulation system 240 of cart 200 via connection assemblies 162 and the passage defined in bottom wall 104. Referring now to FIG. 2, each connection assembly 162 is fluidly connectable to a coupling 164 and self-sealable when disengaged from coupling 164. Coupling 164 is also connectable to a flexible conduit 166 at a first end 168 thereof. Flexible conduit 166 has a second end 172 that is fluidly connectable to port 54 of medical instrument 52. Flexible conduit 166 is operable to direct fluid from coupling 164 through port 54 such that fluid flows through the lumen defined within medical instrument 52. In this manner, medical instrument 52 is connectable to inlet port 159 and to fluid systems of cart 200.

A drain opening 182 is defined through bottom wall 104. Drain opening 182 is preferably located at the lowest point of cavity 108. An outlet port 184 is formed on bottom wall 104 at drain opening 182. Outlet port 184 is external to cavity 108.

A plurality of support structures 178, seen in FIG. 2, is provided within cavity 108 for supporting medical instrument 52. Support structures 178 are attached to either bottom wall 104 or side wall 106 and can be of various shapes in accordance with specific functions. For example, a light conduit 146 (a component of a medical instrument 52) is supported by support structures 178, which are shaped accordingly.

Lid 126 is attachable to tray 102. In the illustrated embodiment, four latchable elements 128 are disposed such that a latchable element 128 is located on each side of lid 126. Latchable elements 128 are dimensioned to engage flange 124 of tray 102 such that lid 126 is attached to tray 102. A vent 132 is defined within lid 126. Vent 132 allows gas to escape from cavity 108 while preventing liquid from escaping from cavity 108 as is conventionally known.

Referring now to cart 200 as shown in FIGS. 1 and 3, cart 200 includes a housing 210. In the illustrated embodiment at least one caster 214 and a traction device 218 are attached to a bottom of housing 210 and dimensioned to support housing 210. A drive means 216 includes a motor (not shown) that is connected to traction device 218 and a steering means (not shown). The steering means is controlled by a controller 300 (discussed further below) and is operable to actuate traction device 218 to direct travel of housing 210. Battery 222 powers drive means 216. Battery 222 is preferably rechargeable. Drive means 216, traction device 218 and the steering means comprise a drive system.

Referring now to FIG. 1, housing 210 of cart 200 is formed to define three receptacles 292a, 292b, and 292c that are each accessible through a front face 288 of housing 210. Each receptacle 292a, 292b, 292c is dimensioned to receive a container 100. Parts, including particular containers 100, associated with a particular receptacle are designated with a letter. For example, parts designated with the letter "a" are associated with receptacle 292a. In this regard, each part that is associated with receptacle 292a is identified with an "a" and is analogous to parts associated with receptacles 292b, 292c that are identified with the letters "b" and "c," respectively. Receptacles 292a, 292b, 292c are generally similar such that receptacle 292b, receptacle 292c, and their associated parts can be understood from a description of receptacle 292a and its associated parts.

Referring still to FIG. 1, receptacle 292a is dimensioned to receive a container 100a. Receptacle 292a includes a pair of spaced-apart, parallel rails 294a disposed such that one rail 294a is disposed on each side of receptacle 292a. Rails 294a are dimensioned to support container 100a. An enclosure 296a is disposed horizontally between rails 294a for enclosing components of circulation system 240, discussed below. In the illustrated embodiment, enclosure 296a is not dimensioned to provide support to container 100a.

As can be seen in FIG. 1, a proximity sensor 298a is disposed within receptacle 292a. Proximity sensor 298a is configured to generate a signal indicative of the presence of container 100a within receptacle 292a. By way of example and not limitation, proximity sensor 298a can be one of the following: a mechanical sensor, an optical sensor, or an electromagnetic sensor.

Referring to FIG. 3, a gas supply conduit 266a is disposed within housing 210 and is connected at a first end to a source for compressed gas (not shown). The compressed gas can be air. A gas supply connector 268a is formed on a second end of gas supply conduit 266a. Gas supply connector 268a is dimensioned to automatically engage and disengage gas supply port 122 of tray 102.

Cart 200 also includes a circulation system 240 that is contained within housing 210 and shown in FIG. 3. Some parts of circulation system 240 are associated with a particular receptacle 292a, 292b, 292c and are designated with an "a," "b," or "c" accordingly. Circulation system 240 includes a first reservoir 246, a second reservoir 248, and a third reservoir 251. In one embodiment, first reservoir 246 stores a fluid such as a washing fluid. Washing fluid is active to treat biological matter coating medical instrument 52. In one embodiment, washing fluid is a pre-cleaning chemistry that is an active chemical solution at a ready-to-use concentration. Second reservoir 248 stores a fluid such as a transporting gel. The transporting gel can be a hydrating gel that is active to prevent drying of biological matter. In one embodiment, the transporting gel is a fluid for preventing the drying and hardening of biological matter on medical instrument 52 stored within container 100a. Third reservoir 251 stores a fluid for rinsing, such as water.

A supply conduit 244 provides for reservoirs 246, 248, and 251 to be fluidly connected with containers 100a, 100b, and 100c, which are respectively located within receptacles 292a, 292b, and 292c. A first end of supply conduit 244 is fluidly connectable to first reservoir 246, second reservoir 248, and third reservoir 251. A first valve 247 controls flow of fluid from first reservoir 246 to supply conduit 244. A second valve 249 controls flow of fluid from second reservoir 248 to supply conduit 244. A third valve 253 controls flow of fluid from third reservoir 251 to supply conduit 244. First valve 247, second valve 249, and third valve 253 are each movable between an open position and a closed position. The open position fluidly connects the associated reservoir to supply conduit 244 and the closed position isolates the associated reservoir from supply conduit 244.

Supply conduit 244 is fluidly connected at a second end to a branch conduit 252a, which is associated with receptacle 292a. In this regard, branch conduit 252a has a first end 254a that is fluidly connected to supply conduit 244. Branch conduit 252a has a second end 256a that is dimensioned to engage inlet port 159 of tray 102. Second end 256a of branch conduit 252a is automatically openable upon being engaged with inlet port 159 and automatically sealable upon being disengaged from inlet port 159. A branch valve 259a, for controlling flow through conduit 252a, is disposed between second end 256a and supply conduit 244. Branch valve 259a is movable between an open position and a closed position. A pump 262, driven by motor 264 (shown schematically in FIG. 3), is disposed within supply conduit 244 between reservoirs 246, 248, and 251 and branch conduit 252a.

Circulation system 240 also includes a primary drain conduit 272 for conducting fluid from receptacles 292a, 292b, 292c to a drain reservoir 276. Primary drain conduit 272 is fluidly connected at a first end to drain reservoir 276, and at a second end to a branch drain conduit 282a, which is associated with receptacle 292a. Branch drain conduit 282a is connected at a first end to drain conduit 272. A connector 258a is formed at a second end of branch drain conduit 282a.

Connector 258a is dimensioned to be fluidly connectable to outlet port 184 of tray 102. In this regard, connector 258a is automatically openable upon being engaged with outlet port 184 and automatically sealable upon being disengaged from outlet port 184. A branch drain valve 284a for controlling flow of fluid through branch drain conduit 282a is disposed in branch drain conduit 282a between drain conduit 272 and connector 258a. Branch drain valve 284a is movable between an open position and a closed position.

With further reference to FIG. 3, a drying system 410, for drying the contents of containers 100a, 100b, 100c, is disposed within housing 200. Some parts of drying system 410 are associated with a particular receptacle 292a, 292b, 292c and therefore are designated with an "a," "b," or "C." Drying system 410 includes a drying conduit 412. Drying conduit 412 has a first end that is fluidly connected to a drying supply conduit 422a and a second end that is fluidly connected to a drying return conduit 462a. A combined dryer and blower unit 414, operable to convey fluid through drying conduit 412 and to remove moisture therefrom, is disposed in drying conduit 412 between drying supply conduit 422a and drying return conduit 462a.

Drying supply conduit 422a has a first end 426a. First end 426a is fluidly connected to branch conduit 252a between valve 259a and second end 256a of branch conduit 252a. A drying supply valve 428a is disposed in drying supply conduit 422a between branch conduit 252a and drying conduit 412. Drying supply valve 428a is movable between an open position and a closed position.

Drying return conduit 462a has a first end 466a that is fluidly connected to branch drain conduit 282a between branch drain valve 284a and connector 258a. A return conduit valve 468a is disposed in return conduit 462a between drying conduit 412 and branch drain conduit 282a. Return conduit valve 468a is movable between an open position and a closed position.

Referring to FIGS. 1 and 3, housing 210 includes a horizontal top panel 232 that has a user interface 234, a radio frequency identification (RFID) receiver/transmitter 239, and a controller 300 disposed therein. User interface 234 includes a visual indicator 236, e.g., a display screen, as is commonly known. User interface 234 also includes an input means 238, such as an alphanumeric keypad. RFID receiver/transmitter 239 is operable to determine an identity of container 100 as indicated by a RFID tag 241 disposed on container 100. RFID transmitter 239 is configured to generate a first signal indicative of the identity of a container 100 in accordance with RFID tag 241.

Controller 300 is schematically illustrated in FIG. 3 and is a microprocessor or micro-controller that is programmed to control the operation of cart 200. Controller 300 is electrically connected to first valve 247, second valve 249, third valve 253, branch conduit valve 259a, drain valve 284a, supply conduit valve 428a, return conduit valve 468a, combined dryer and blower unit 414, drive means 216, user interface 234, proximity sensor 298a, and REID transmitter 239 (electrical connections not shown).

Controller 300 is programmed to use the signal generated by proximity sensor 298a to determine when container 100a is disposed within receptacle 292a. Controller 300 is also programmed to determine an identity of container 100 in accordance with the first signal provided by RFID transmitter 239. Alternatively, a container 100 is identified by a conventionally known means, such as a bar code system. Controller 300 is also configured to communicate with a master computer 310 (shown schematically on FIG. 4), and controller 300 includes a first data storage means.

Master computer 310 comprises a central information system. Master computer 310 is programmed to provide instructions to cart 200 and includes a second data storage means for storing status information. By way of example and not limitation, status information can be related to: the location of cart 200, if a container 100 is disposed within receptacle 292, the particular receptacle 292 in which a container 100 is disposed, the identification of any container 100 disposed therein, the time when container 100 was placed into or removed from housing 210, the treatment status of container 100, and other information regarding container 100 or the instruments therein.

The present invention will now be further described with respect to operation of transport device 10. Operation of transport device 10 includes a treatment aspect and a transport aspect. For clarity, the following description of the operation of transport device 10 refers to container 100*a* as it relates to receptacle 292*a* of cart 200, as shown in FIG. 3. It should be appreciated that the operation described below can be adapted to apply to receptacles 292*b*, 292*c* and containers 100*b*, 100*c*.

Prior to transport or treatment by transport device 10, a medical instrument 52 is placed within cavity 108 of tray 102. As indicated above, when disposed within cavity 108, lumens and passageways within medical instrument 52 are connected to the passage defined within bottom wall 104.

Medical instrument 52 is connected to the passage defined within bottom wall 104 by fluid connection of a coupling 164 to a connection assembly 162 of bottom wall 104. First end 168 of a flexible conduit 166 is fluidly connected to coupling 164. Second end 172 of flexible conduit 166 is fluidly connected to port 54 on medical instrument 52. In this manner, a lumen within medical instrument 52 is fluidly connected to inlet port 159 of tray 102. It should be appreciated that the order in which the various components are connected, i.e., engaged, can be varied without affecting the operation of transport device 10. After medical instrument 52 is placed within cavity 108 and connected to the passage within bottom wall 104, lid 126 is placed over tray 102 such that cavity 108 is covered. Then, latchable elements 128 are engaged with flange 124 of tray 102 to secure lid 126 to tray 102 thereby closing container 100*a*.

Closed container 100*a* is inserted into receptacle 292*a* of cart 200 such that cart 200 receives and retains container 100*a*. All valves associated with receptacle 292*a*, i.e., branch conduit valve 259*a*, drain valve 284*a*, supply conduit valve 428*a*, and return conduit valve 468*a* are in a closed position before container 100*a* is inserted into receptacle 292*a*. Preferably, as container 100*a* is inserted into receptacle 292*a*, inlet port 159 of tray 102 automatically engages second end 256*a* of branch conduit 252*a* and outlet port 184 of tray 102 automatically engages connector 258*a*. In addition, gas supply port 122 automatically engages gas supply connector 268*a*. In this manner, container 100*a* is fluidly connected to the systems of cart 200.

Controller 300 determines that container 100*a* is disposed within receptacle 292*a* by using the signal generated by proximity sensor 298*a*. In addition, controller 300 receives a signal from RFID transmitter 239 that indicates the identity of container 100*a*. In one embodiment, whether container 100*a* is disposed within receptacle 292*a* and the identity of container 100*a* disposed within receptacle 292*a* comprise status information that is communicated to master computer 310. It should be appreciated that status information could be stored by controller 300 in first data storage means for later use by controller 300. Status information stored by controller 300 can also be retrieved at a later time by hospital staff via user interface 234 or transferred to master computer 310 at a later time.

According to the treatment aspect of the present invention, cart 200 is operable to expose medical instruments disposed within container 100*a* to a treatment cycle. During a typical treatment cycle, a fluid is introduced into container 100*a* such that the fluid contacts the exterior surfaces and the interior surfaces of medical instruments contained therein. Preferably, the fluid is a washing fluid contained within first reservoir 246 and the washing fluid is a pre-cleaning chemistry as described above. It is appreciated that the washing fluid can be water or a concentrated chemical solution for cleaning that is diluted by water prior to use. If the washing fluid is a concentrated chemical solution for cleaning, then metering pumps (not shown) are provided to dilute the concentrated chemical solution for cleaning to a predetermined concentration using water. It should be appreciated that water for dilution could be stored in third reservoir 251 or in an additional reservoir (not shown).

Referring now to a treatment cycle in one embodiment, after container 100*a* is inserted into receptacle 292*a*, hospital staff cause controller 300 to initiate a treatment cycle via input mechanism 238 of user interface 234. To begin a treatment cycle, controller 300 causes inflatable seal 116 to inflate by operating the source for compressed gas. When inflatable seal 116 has been inflated, inflatable seal 116 contacts lid 126 and channel 114 such that cavity 108 is hermetically sealed. In this regard, inflatable seal 116 forms a microbial barrier when inflated.

After inflatable seal 116 has been inflated, controller 300 opens first valve 247 and branch conduit valve 259*a* and actuates motor 264 to operate pump 262 such that washing fluid is introduced into cavity 108 from first reservoir 246. In one embodiment, the washing fluid is a pre-cleaning chemistry. Washing fluid is directed into cavity 108 through spray nozzles 156. Washing fluid is also conducted through flexible connector 166 into the lumen within medical instrument 52. In one embodiment, washing fluid is allowed to fill cavity 108 of tray 102. Cavity 108 is determined to be fully by means well understood in the art.

After washing fluid has filled cavity 108, controller 300 closes first valve 247 and branch conduit valve 259*a* and deactivates pump 262 such that flow of washing fluid into cavity 108 ceases. Then, controller 300 initiates a timer such that washing fluid is retained within cavity 108 for a predetermined exposure period. After the predetermined exposure period has elapsed, controller 300 actuates branch drain valve 284*a*, such that washing fluid flows from cavity 108 through drain branch conduit 282*a* and drain conduit 272 into drain reservoir 276. After washing fluid is drained from cavity 108, controller 300 closes branch drain valve 284*a*.

After washing fluid has been drained from cavity 108, controller 300 opens second valve 249 and branch conduit valve 259*a*, and activates pump 262, such that transporting gel is introduced into cavity 108. In one embodiment, the transporting gel is a hydrating gel that is active to prevent drying of biological matter. Transporting gel flows from second reservoir 248 through supply conduit 244 and branch conduit 252*a* into cavity 108. The flow of the transporting gel is similar to that discussed above regarding the flow of washing fluid into container 100*a*. In this respect, the transporting gel is directed into cavity 108 of tray 102 through spray nozzles 156 and through the lumen defined in medical instrument 52. After the transporting gel is introduced into cavity 108, controller 300 closes second valve 249 and branch conduit valve 259*a* and deactivates pump 262 such that flow of transporting gel into cavity 108 ceases. According to one embodiment, transporting gel is allowed to remain in container 100*a* until reprocessing of medical instrument begins. The treatment aspect of transport device 10 is complete when reprocessing begins.

Alternatively, after washing fluid has been drained from cavity 108, controller 300 opens third valve 253 and branch conduit valve 259*a* and actuates motor 264 to operate pump 262 such that rinsing fluid is introduced into cavity 108 from third reservoir 251. In one embodiment, the rinsing fluid is water. Rinsing fluid is directed into cavity 108 through spray nozzles 156. Rinsing fluid is also conducted through flexible connector 166 into the lumen within medical instrument 52. In one embodiment, rinsing fluid is allowed to fill cavity 108 of tray 102.

After rinsing fluid has filled cavity 108, controller 300 closes third valve 253 and branch conduit valve 259a and deactivates pump 262 such that flow of rinsing fluid into cavity 108 ceases. Then, controller 300 initiates a timer such that rinsing fluid is retained within cavity 108 for a predetermined exposure period. After the predetermined exposure period has elapsed, controller 300 actuates drain valve 284a such that rinsing fluid flows from cavity 108 through drain branch conduit 282 into drain reservoir 276. It should be appreciated that third valve 253, branch conduit valve 259a, and branch drain valve 284a can be in their respective open positions while pump 262 is active such that rinsing fluid flows continuously from third reservoir 251 to drain reservoir 276 for a predetermined period of time.

After the rinsing fluid is drained from cavity 108, controller 300 closes branch drain valve 284a and activates drying supply conduit valve 428a and drying return conduit valve 468a of drying system 410 such that both valves are in their respective open positions. Controller 300 then activates combined dryer and blower unit 414. Combined dryer and blower unit 414 recirculates a gas through drying conduit 412 and container 100a to effect drying of the gas therethrough as is conventionally known. In this manner, moisture is removed from cavity 108 of tray 102 and medical instrument 52 is dried.

Referring now to the transporting aspect of the operation of the present invention, cart 200 is operable as an automated guided vehicle (AGV) to automatically transport a container 100 from a first location to a second location. It should be appreciated that the transport aspect of the present invention can be performed independently of the treatment aspect of the present invention. In other words, transport of container 100 can occur before, during, or after treatment of medical instrument 52 within container 100.

The operation of the transporting aspect of the present invention will now be described in detail with reference to FIG. 4. In one embodiment, cart 200 is summoned to procedure room 18. Preferably, hospital staff summon cart 200 by activating a signaling means (not shown). The signaling means is electrically linked, or networked, to master computer 310 and may be a computer terminal or other input device.

Figure 4:
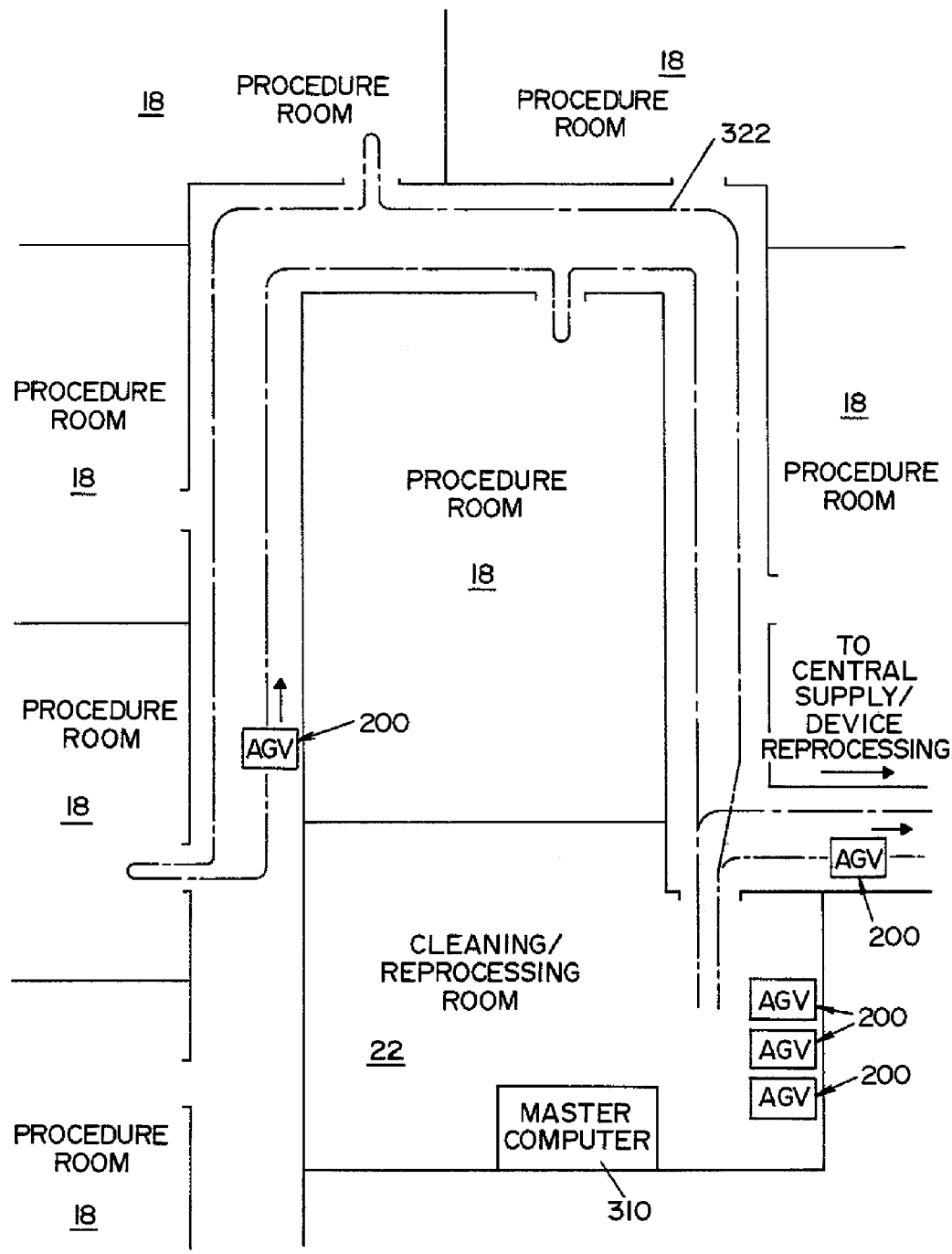
FIG. 4 is a pictorial illustration showing a transportation route for a transport device.

Cart 200 travels along a pathway or route 322 as shown in FIG. 4. The route includes a cleaning room 22 and one or more procedure rooms 18. After container 100 is placed within cart 200, cart 200 departs from the procedure room. In the illustrated embodiment, cart 200 returns directly to cleaning room 22. It is appreciated that cart 200 could be directed to proceed other procedure rooms and pick up additional containers 100 prior to returning to cleaning room 22.

Alternatively, cart 200 can arrive at procedure room 18 in the course of a regular circuit of route 322. In this case, when cart 200 arrives at procedure room 18, hospital staff acknowledge the presence of cart 200 via user interface 234 and insert container 100 having medical instrument 52 contained therein into one of receptacles 292a, 292b, 292c. It is further appreciated that hospital staff can acknowledge cart 200 by utilizing user interface 234 such that cart 200 leaves procedure room 18 without having container 100a inserted therein.

In one embodiment, hospital staff terminates any ongoing treatment cycle via user interface 234 after cart 200 arrives at cleaning room 22 with container 100a. Container 100 is then removed from cart 200. Controller 300 is programmed to detect that container 100 has been removed from a receptacle 292 using the signal generated by one of proximity sensors 298a, 298b, 298c and to indicate via visual indicator 236 that container 100a has been removed. Preferably, controller 300 communicates the status of cart 200 and container 100 to master computer 310. By way of example and not limitation, the status of container 100 can include the following information: the time that container 100 was delivered to cleaning room 22, whether 100 container has been delivered to cleaning room 22, whether a treatment cycle has been performed, and where container 100 is to be delivered after reprocessing is complete. After removal of container 100 from cart 200, cart 200 returns to a staging area or continues along route 322 as described above.

After removal of container 100 from cart 200, medical instrument 52 disposed within container 100 is cleaned and reprocessed according to cleaning and reprocessing methods known in the art. After reprocessing, medical instrument 52 is dried and stored in sterile conditions. When medical instrument 52 is required for use during a procedure it can be placed within a container 100. Container 100 is then inserted into cart 200 and transported to a procedure room 18. Upon arrival at the second procedure room, container 100 is removed from receptacle 292a, and controller 300 communicates an update regarding the status of container 100 to main computer 310.

Alternatively, the contents of container 100 are not dried after reprocessing and are wet when transported by cart 200 to a procedure room according to just-in-time (JIT) principles as are conventionally known.

In an alternative embodiment, container 100a is placed in a receptacle 292a, and fluid is introduced into cavity 108 before seal 116 is inflated such that fluid overflows tray 102. In this embodiment, means for capturing fluid (not shown) as it overflows is provided within housing 210. In addition, means for directing the captured fluid to drain reservoir 276 is provided.

In another alternative embodiment, medical instrument 52 has an optic/electronic channel defined therethrough. The optic/electronic channel is a passageway through which electrical and optical components pass. The optic/electronic channel is dimensioned to protect such components from the potentially harmful effects of contact with fluids. Leak testing of optic/electronic channels defined within the medical instruments can be done after liquids have been drained from cavity 108. In one embodiment, valves, fittings, pressure indication, and compressors are provided such that leak testing can be performed automatically according to a treatment cycle and governed by controller 300. Leak testing would be performed according to known methods.

In still another alternative embodiment (not shown), conduit and connectors are provided in circulation system 240 for allowing recirculation through supply conduit 244 and at least one container 100.

The foregoing descriptions are specific embodiments of the present invention. It should be appreciated that these embodiments are described for purposes of illustration only and that those skilled in the art may practice numerous alterations and modifications without departing from the spirit and scope of the invention. It is intended that all such modifications and alterations be included insofar as they come within the scope of the invention as claimed or the equivalents thereof.

Having described the invention, the following is claimed:

1. A mobile device for transporting at least one medical instrument from a first location to a second location while maintaining said at least one medical instrument in a moist environment prior to said at least one medical instrument being cleaned at said second location, comprising:
- a container including:
  - a cavity dimensioned to receive at least one medical instrument, and
  - a first opening for providing fluid access to said cavity; and
- a cart including:
  - a receptacle for receiving said container, wherein said container is dimensioned for insertion into and removal from said receptacle,
  - a circulation system for supplying a fluid to said container, said circulation system including:
    - a reservoir for storing a fluid, and
    - a supply conduit having a first end fluidly connected to said reservoir and a second end fluidly connectable to said first opening of said container,
  - a controller configured to receive a signal from an operator to summon said cart wherein said cart travels along a pathway from said first location to said second location,
  - a drive system connected to said controller, said drive system including:
    - a traction device for supporting said cart and for propelling said cart, and
    - a steering device for directing travel of said cart based on said commands received from said controller, and
  - a power system for supplying power to said drive system and said controller,
  - wherein said controller is programmed to control said drive system and said circulation system to move said cart along said pathway while conveying said fluid to said container.

2. A mobile device according to claim 1, wherein said medical instrument has a lumen defined therein, and said lumen of said medical instrument is fluidly connected to said first opening of said container.

3. A mobile device according to claim 1, wherein said circulation system further comprises:
- a drain conduit fluidly connectable at one end to a second opening of said container and fluidly connected at another end to a drain reservoir.

4. A mobile device according to claim 3, further comprising a drying system, said drying system including:
- a drying conduit fluidly connectable at one end to said second opening of said container and fluidly connectable at another end to said first opening of said container;
- a blower for conveying air through said drying conduit and through said cavity of said container; and
- a dryer for removing moisture from said air conveyed through said drying conduit.

5. A mobile device according to claim 1, wherein said fluid is a transporting gel.

6. A mobile device according to claim 5, wherein said transporting gel is a hydrating gel for adding moisture to biological matter disposed on said medical instrument.

7. A mobile device according to claim 1, further comprising:
- a pump for conveying said fluid between said at least one reservoir and said cavity of said container.

8. A mobile device as defined in claim 1, wherein said controller includes input means for allowing a user to input data indicative of said second location into said controller.

9. A mobile device as defined in claim 1, wherein said controller includes wireless communication means for communicating with a master computer, said controller receiving data indicative of said second location from said master computer.

10. A mobile device as defined in claim 1, further comprising:
- a sensor configured to generate a signal indicative of the presence of said container within said receptacle, said controller connected to said sensor to receive said signal.

11. A mobile device for transporting at least one medical instrument from a first location to a second location while maintaining said at least one medical instrument in a moist environment prior to said at least one medical instrument being cleaned at said second location, comprising:
- a container including:
  - a cavity dimensioned to receive at least one medical instrument, and
  - a first opening and a second opening for providing fluid access to said cavity, and
- a cart including:
  - a receptacle for receiving said container, wherein said container is dimensioned for insertion into and removal from said receptacle,
  - a circulation system for supplying a fluid to said container, said circulation system including:
    - a first reservoir for storing a first fluid,
    - a second reservoir for storing a second fluid,
    - a drain reservoir for receiving said first and second fluids,
    - a supply conduit having a first end fluidly connectable to said first reservoir and said second reservoir and a second end fluidly connectable to said first opening of said container, and
    - a drain conduit having a first end fluidly connectable to said second opening of said container and a second end fluidly connected to said drain reservoir,
  - a controller configured to receive a signal from an operator to summon said cart wherein said cart travels along a pathway from said first location to said second location,
  - a drive system connected to said controller, said drive system including:
    - a traction device for supporting said cart and for propelling said cart, and
    - a steering device for directing travel of said cart based on said commands received from said controller, and
  - a power system for supplying power to said drive system and said controller,
  - wherein said controller is programmed to control said drive system and said circulation system to move said cart along said pathway while conveying said first and second fluids to said container.

12. A mobile device according to claim 11, wherein said first fluid is a washing fluid.

13. A mobile device according to claim 11, wherein said second fluid is a rinsing fluid.

14. A mobile device according to claim 11, further comprising a drying system, said drying system including:
- a drying conduit fluidly connectable at one end to said second opening of said container and fluidly connectable at another end to said first opening of said container;
- a blower for conveying air through said drying conduit and through said cavity of said container; and
- a dryer for removing moisture from said air conveyed through said drying conduit.

* * * * *